(12) United States Patent
Bottini et al.

(10) Patent No.: US 8,399,213 B2
(45) Date of Patent: Mar. 19, 2013

(54) METHOD FOR MONITORING INTRACELLULAR TYROSINE PHOSPHATASE ACTIVITY

(75) Inventors: Nunzio Bottini, San Diego, CA (US); Stephanie Stanford, San Diego, CA (US); Amy Barrios, Salt Lake City, UT (US); Sayantan Mitra, San Diego, CA (US)

(73) Assignee: University of Southern California, Los Angeles, CA (US)

( * ) Notice: Subject to any disclaimer, the term of this patent is extended or adjusted under 35 U.S.C. 154(b) by 440 days.

(21) Appl. No.: 12/571,301

(22) Filed: Sep. 30, 2009

(65) Prior Publication Data

US 2010/0086957 A1 Apr. 8, 2010

Related U.S. Application Data

(60) Provisional application No. 61/101,620, filed on Sep. 30, 2008.

(51) Int. Cl.
*C12Q 1/42* (2006.01)

(52) U.S. Cl. ............................................. 435/21; 435/15

(58) Field of Classification Search .................... 435/21, 435/15; 530/350
See application file for complete search history.

(56) References Cited

U.S. PATENT DOCUMENTS

| | | | |
|---|---|---|---|
| 5,998,593 A * | 12/1999 | Huff et al. ...................... | 536/4.1 |
| 6,329,137 B1 | 12/2001 | Cromlish et al. | |
| 2002/0068301 A1 | 6/2002 | Lai et al. | |
| 2005/0100951 A1 | 5/2005 | Pircher | |
| 2007/0031892 A1* | 2/2007 | Barrios et al. ................. | 435/7.1 |

OTHER PUBLICATIONS

Mitra S. et al. A Series of Peptide Based Fluorogenic Probes for PTP Activity. Analytical Biochemistry 370(2007)249-251.*
Mitra S. et al. Highly Sensitive Peptide Based Probes for PTP Activity . . . Bioorganic & Medicinal Chemistry Letters 15(2005)5142-5145.*
Knight C. G. A Quenched Fluorescent Substrate for Thimet Peptidase Containing a New Fluorescent Amino Acid . . . Biochemistry J 274:45-48, 1991.*
Angewandte Chemie Supporting Information for Angew. Chem. Int. Ed. Z54116 *Angewandte Chemie* Wiley-VCH 2004; Weinheim, Germany 69451.
Wanda A. Cromlish, et al.; *Development and Validation of an Intact Cell Assay for Protein Tyrosine Phosphatases Using Recombinant Baculoviruses*; Biochemical Pharmacology, vol. 58, pp. 1539-1546, (1999).
Kevin G. Peters, et al.; *Mechanism of Insulin Sensitization by BMOV (bis maltolate oxo Vanadium); Unliganded Vanadium ($VO_4$) As the Active Component*; Journal of Inorganic Biochemistry 96 (2003) 321-330.

* cited by examiner

*Primary Examiner* — Ralph Gitomer
(74) *Attorney, Agent, or Firm* — DLA Piper LLP (US)

(57) ABSTRACT

The invention relates in general to tyrosine dephosphorylation. More specifically, the invention relates to methods and compositions for monitoring intracellular tyrosine dephosphorylation at the single cell level. The invention further relates to techniques that can be used as aid in the development of novel therapeutics, and monitor regulation of intracellular tyrosine phosphatase activity at the single cell level.

6 Claims, 9 Drawing Sheets

METHOD FOR MONITORING INTRACELLULAR TYROSINE PHOSPHATASE ACTIVITY

CROSS-REFERENCE TO RELATED APPLICATIONS

The present application claims the benefit of the filing date of U.S. Provisional Application No. 61/101,620 filed Sep. 30, 2008, the disclosure of which is incorporated herein by reference in its entirety.

STATEMENT REGARDING FEDERALLY SPONSORED RESEARCH OR DEVELOPMENT

This invention was made with government support under Contract No. R21 GM079386 awarded by the National Institutes of Health. The government has certain rights in the invention.

SEQUENCE LISTING

This application contains sequence listing.

FIELD OF THE INVENTION

The present invention relates in general to tyrosine dephosphorylation. More specifically, the invention provides methods for monitoring tyrosine phosphatase activity in cells.

BACKGROUND OF THE INVENTION

Tyrosine phosphorylation is a key regulatory and signaling mechanism utilized by cells.[1] In cells, tyrosine phosphorylation is dynamic, with phosphorylation by protein tyrosine kinases (PTKs) and dephosphorylation by protein tyrosine phosphatases (PTPs) occurring in concert under exquisite cellular control.[2] Misregulated tyrosine phosphorylation of key signaling molecules is involved in a number of disease states, including autoimnunity and cancer.[3,4] For example, one vital biological process in which tyrosine phosphorylation is crucial is T cell receptor (TCR) signaling. T cell function is both positively and negatively regulated by reversible tyrosine phosphorylation. One of the first steps following binding of an antigen to the TCR is the activation of Lck, a Src family PTK.[5] Lck is positively regulated through phosphorylation of Y394 and negatively regulated through phosphorylation of Y505.[5,6] Relatively minor changes in the PTP/PTK balance can have a major impact in TCR signaling and result in immunological diseases including autoimmunity, allergies and immunodeficiency.[6] Although it is clear that tyrosine phosphorylation is crucial in regulating cellular signaling and that PTPs and PTKs are key targets in the treatment of many human diseases, researchers have not yet assembled the toolbox necessary to thoroughly characterize and fully assess the regulation of these enzymes in single cells. Indeed, it has been recently recognized that one of the major challenges in the field of phosphorylation-dependent signal transduction is the lack of techniques capable of dynamic and single-cell analysis of intracellular phosphorylation and dephosphorylation.[7]

Despite the importance of reversible tyrosine phosphorylation in many cellular processes, techniques for detecting and measuring tyrosine phosphorylation have been relatively slow to develop. Currently, a number of phospho-tyrosine analogs are available for in vitro phosphatase assays, including small, non-peptidic substrates such as para-nitrophenylphosphate (p-NPP), 4-methylumbelliferone phosphate (MUP) and its fluorinated derivative difluoromethylumbelliferone phosphate (DiFMUP).[8] For some time, intracellular protein tyrosine phosphorylation was exclusively detected using radio-labeling methods.[9] More recently the development of anti-phospho-tyrosine[10] and of specific anti-phospho-residue[11] antibodies allowed for the development of western blotting techniques. These antibodies are also used in microscopy to characterize the spatial distribution of tyrosine phosphorylation inside cells.[12] Despite the advancement in techniques, the field still suffers from lack of detection methods capable of dynamic and single-cell level analysis of tyrosine phosphorylation. Similar methods are already available for other signaling phenomena. For example, real-time single-cell analysis of intracellular calcium waves is now possible both in flow cytometry and microscopy using special calcium-sensitive fluorescent probes.[13] Although PTPs are promising drug targets, the lack of adequate methods for monitoring their intracellular activity has limited the development of cell-based assays for screening of PTP inhibitors. A common challenge of developing anti-PTP small molecule inhibitors for therapy of human diseases has been so far the low cell-permeability of inhibitor lead compounds. A cell-based assay of PTP activity would help selecting cell-permeable enzyme inhibitors, and would be particularly helpful in speeding up development of novel anti-PTP therapies for a variety of human diseases.

SUMMARY OF THE INVENTION

The inventors have discovered a new method for monitoring intracellular tyrosine dephosphorylation. This technique can be used to aid in the development of new therapeutics, and for studying the regulation of protein tyrosine phosphatases in single cells, among other applications.

PTPs are emerging as important drug targets for inflammation, cancer and metabolic diseases.[3,4] Known PTPs that have been implicated in disease are: PTPN22 (autoimmunity); LMPTP (diabetes and cancer); PTP1B (diabetes and obesity); SHP2 and PRL3 (cancer); and STEP (Alzheimer's).[18] The inventors have focused on the development of new peptide-based in vitro PTP assays, as well as cell-based assays for the development of highly specific, cell-permeable PTP inhibitor leads. Examples shown of new phosphatase assays developed by the inventors make use of a recently developed fluorescent tyrosine analog, coumaryl-amino propionic acid (CAP).[15] CAP can be synthesized in a phosphorylated form (pCAP), which can be incorporated into peptides. PTPs recognize pCAP-peptides as substrates, and hydrolyze them into CAP-peptides. Upon excitation at 340 nm, CAP-containing peptides are over $10^4$ times more fluorescent than pCAP-containing peptides (emission wavelength=460 nm).[15] Hydrolysis of pCAP peptides yields a continuous, direct, fluorescent phosphatase assay. The inventors determined that pCAP peptides are suitable substrates for PTPs, and have developed in vitro and cell-based assays for tyrosine phosphatase activity. The approach used to detect dephosphorylation of pCAP peptides can be easily applied to any cell-permeable fluorescent substrate, of peptidic or non-peptidic nature.

In one embodiment, the invention relates to methods and compositions of detecting intracellular PTP activity. The methods comprise obtaining phosphorylated coumaryl-amino propionic acid (pCAP) containing peptides, internalizing the peptides into cells, and detecting PTP intracellular activity by monitoring cell fluorescence of the cells.

In another embodiment, the invention relates to methods and compositions for monitoring intracellular PTP activity by flow cytometry. The methods comprise internalizing fluorescent PTP substrates into cells and monitoring intracellular PTP activity by visualizing cell fluorescence of the cells with a flow cytometer.

In a related embodiment, the invention relates to methods and compositions for monitoring intracellular PTP activity by fluorescence microscopy. The methods comprise internalizing fluorescent PTP substrates into suspension cells and monitoring intracellular PTP activity by visualizing cell fluorescence of the cells with a fluorescence microscope.

In accordance with another embodiment, the invention relates to methods and compositions of cell-based high-throughput screening for PTP inhibitors. The methods comprise internalizing fluorescent PTP substrates into cells, monitoring intracellular PTP activity of the cells by detecting cell fluorescence by flow cytometry or fluorescence microscopy, monitoring the amount of the inhibition of PTP activity of the cells by FACS or microscopy analysis, and determining that the amount of PTP activity of a control cell is greater than the PTP activity of the cells is indicative of a PTP inhibitor.

In yet another embodiment, the invention relates to cell permeable peptides for use in intracellular PTP activity detection. The peptide comprise pCAP or fluorinated derivative fused to a cell penetrating peptide (CPP) or other cell permeable tags.

In accordance with another embodiment, the invention relates to methods and compositions of cell-based high-throughput screening for PTP inhibitors.

The above-mentioned and other features of this invention and the manner of obtaining and using them will become more apparent, and will be best understood, by reference to the following description, taken in conjunction with the accompanying drawings. The drawings depict only typical embodiments of the invention and do not therefore limit its scope.

DETAILED DESCRIPTION OF THE INVENTION

The inventors developed methods based on flow cytometry and fluorescence microscopy to detect intracellular dephosphorylation of a fluorescent PTP substrate in cells incubated with said substrate. The inventors tested this method using pCAP peptides, which have several characteristics that make them more suited than traditional fluorescent non-peptidic substrates (for example DifMUP) to single-cell detection of PTP activity. Peptide substrates show some enzyme specificity and can be used to detect the intracellular activity of a single or a few PTPs. pTyr peptides cannot be used for this scope since the detection approach used for pTyr peptides is incompatible with single-cell assays, thus preventing the use of pTyr peptides in a cell-based assay for PTP inhibitors. The inventors developed a highly sensitive continuous, peptide-based assay which is ideal for intracellular detection of PTP activity. Such an assay also provides a high-throughput method to rapidly screen for PTP inhibitors, providing lead compounds that are already optimized for cell permeability, minimal cellular toxicity, and enzyme specificity. Although optimized for pCAP peptides, the flow cytometry and fluorescence microscopy-based methods developed by the inventors will work as well with non peptidic fluorescent substrates, for example DifMUP and similar compounds, after the appropriate optimization steps have been taken.

Figure 7:
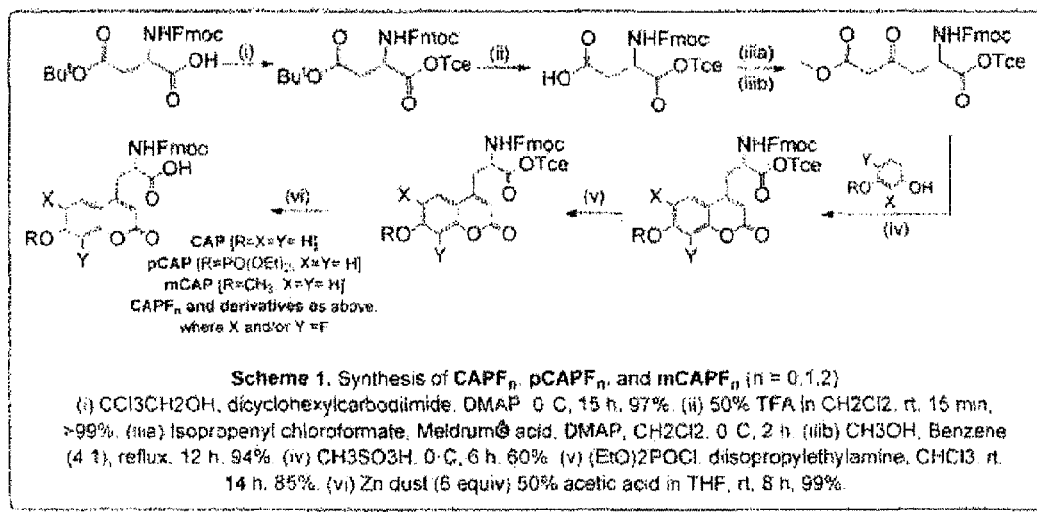
FIG. 7 shows a schematics of the synthetic pathways for synthesizing an enantiometrically pure coumaryl amino propionic acid and its fluorinated derivatives.

The syntheses of enantiomerically pure coumaryl amino propionic acid (CAP), methoxy-CAP (mCAP), phosphorylated CAP (pCAP) and fluorinated derivatives in high yield from inexpensive commercially available starting materials are shown in FIG. 7.[14, 15]

Figures 1A, 1B:
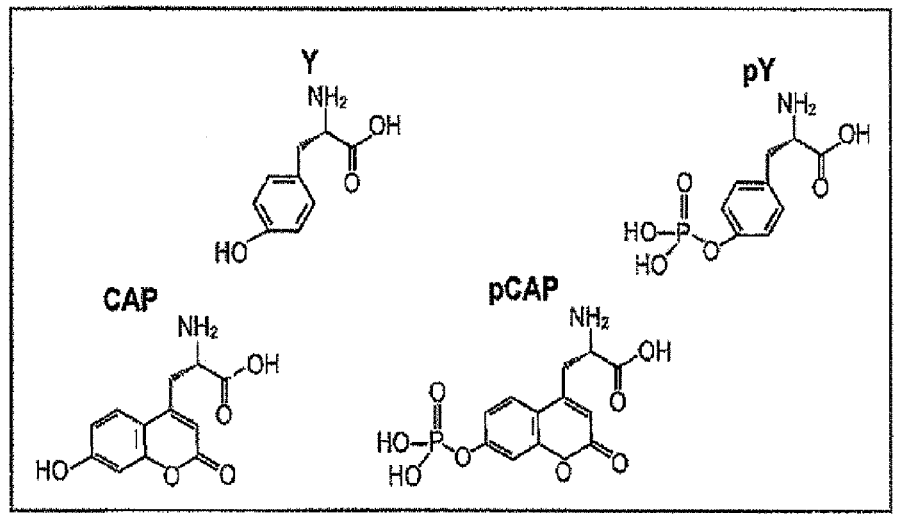
FIG. 1. pCAP peptides are good substrates for PTPs, but are not dephosphorylated by serine phosphatases. (A) Structure of CAP, pCAP, and Et2-pCAP, a non-hydrolyzable form of pCAP. (B) Kinetic parameters of dephosphorylation of 9LckpCAP394 peptide by PTPN22. (C) Time-course of dephosphorylation of 0.2 mM 9LckpCAP394 peptide by PP1 (filled triangles), PP2A (open squares), or PP2B (filled squares). Linear regression is also shown. The activity of the enzymes was normalized using difluoromethylumbelliferone phosphate (DiFMUP) as substrate and equal units were used for all the assays on pCAP peptide. Open diamonds and dashed line show representative activity of all enzymes on 0.2 mM DiFMUP.
Figure 1C:
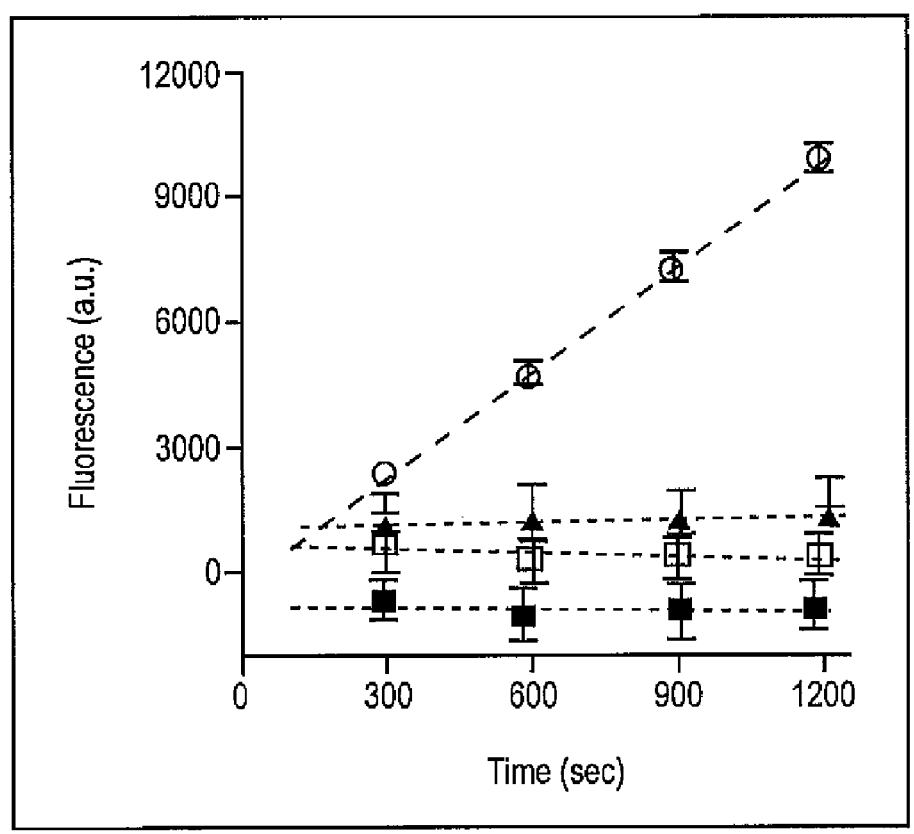
Figure 2:
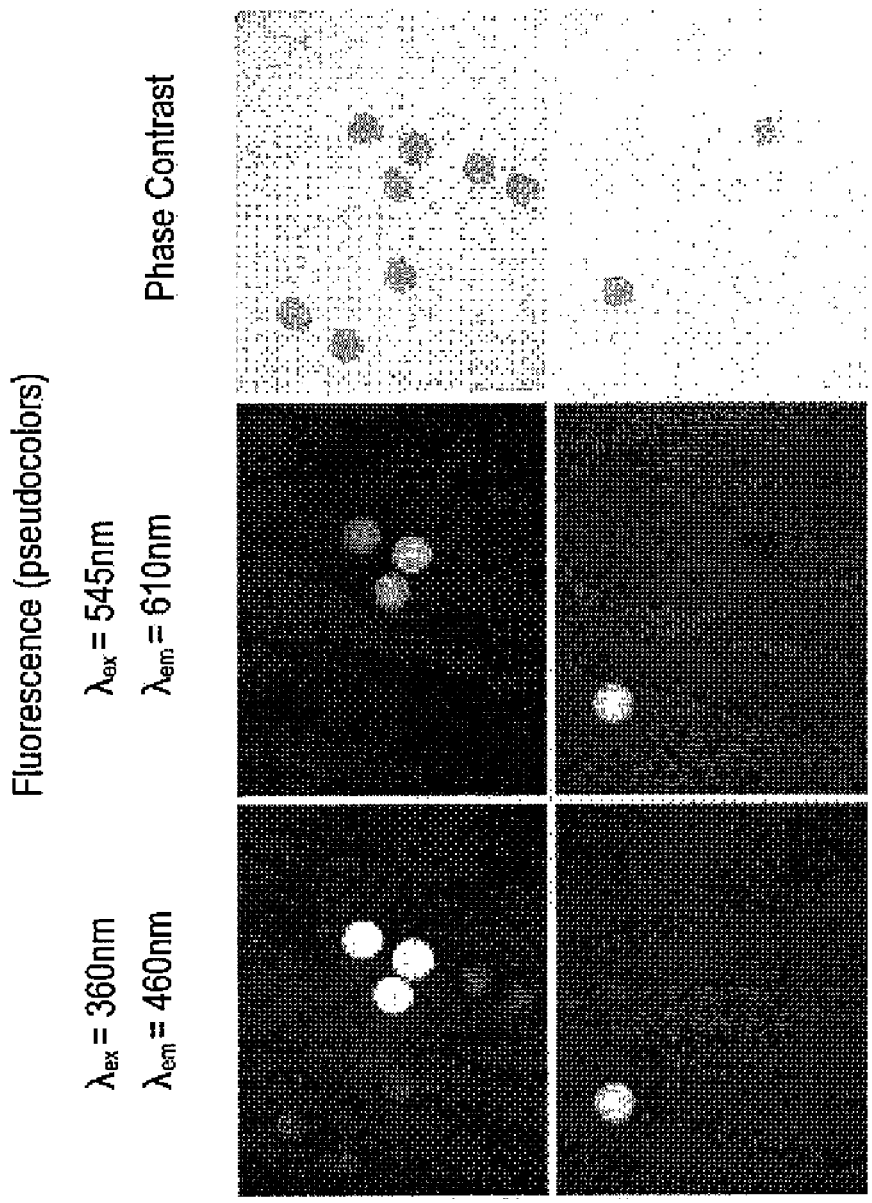
FIG. 2. Dephosphorylation of pCAP peptide by intracellular PTPs after microinjection. Images of microinjected sea urchin eggs were taken after injection on a fluorescence microscope. Cells were injected with 9LckpCAP394 peptide dissolved in DMSO (upper panels) or in DMSO containing vanadate (lower panels). To correct for cell/injection volumes, and as an injection marker, fixed amounts of rhodamine were co-injected with the peptides. Left panels shows cell fluorescence as detected using a DAPI cube. Middle panels shows cell fluorescence as detected using a rhodamine cube. Right panels show phase contrast microscopy.
Figures 3A, 3B:
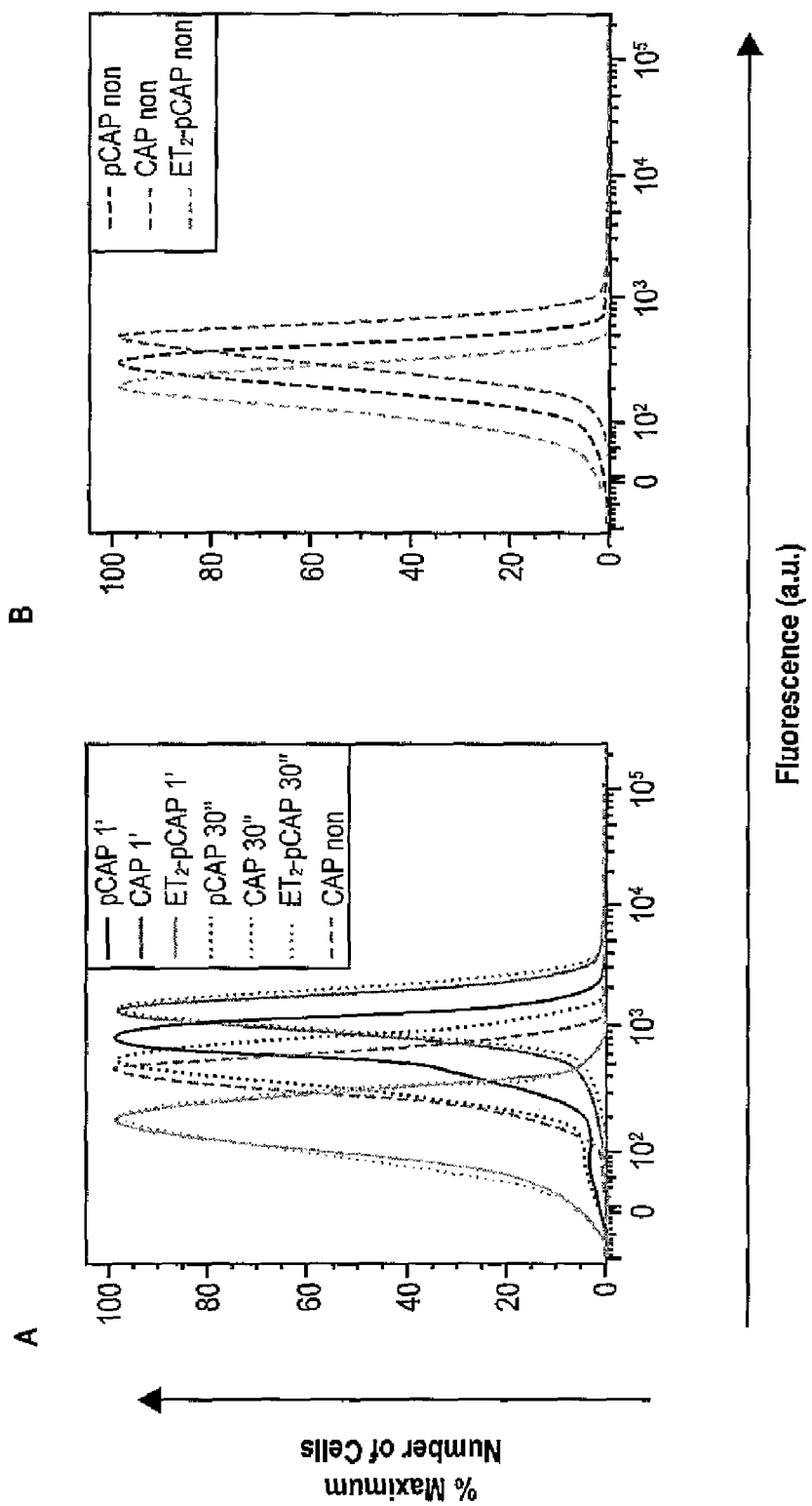
FIG. 3. Dephosphorylation of pCAP peptide by intracellular PTPs after nucleofection. (A) Time-course of intracellular dephosphorylation of nucleofected 9Lck394 CAP-based peptides. JTAg human T cells were nucleofected in the presence of 100 µM pCAP peptide (blue lines), 100 µM CAP peptide (red lines) or 100 µM of a non-hydrolyzable Et2pCAP peptide (green lines). Cell fluorescence was measured using a BD LSR-II with a DAPI filter at 30" (dotted lines) and 1' (continuous lines). The dashed red line shows fluorescence of non-nucleofected cells incubated with 100 µM CAP peptide. (B) Fluorescence of non-nucleofected JTAg cells incubated in the presence of the CAP-based peptides used for the experiment in panel (A). Graphs show fluorescence of non-nucleofected cells incubated with 100 µM pCAP peptide (dashed blue line), 100 µM CAP peptide (dashed red line) or 100 µM of a non-hydrolyzable Et2pCAP peptide (dashed green line). Data from panel (A) and (B) are representative of the same experiment. (C) Longer time-course of intracellular dephosphorylation of nucleofected pCAP peptide. JTAg cells were nucleofected in the presence of 100 µM 9LckpCAP394 peptide and cell fluorescence was measured at 1' (pink line), 2.5' (purple line), 5' (light blue line), and 10' (dark blue line). Red line shows fluorescence of JTAg cells at 10' after nucleofection in the presence of 100 µM 9LckCAP394. Blue dotted line shows fluorescence of non-nucleofected JTAg cells incubated in the presence of 100 µM of the pCAP peptide. 9LckX394 peptide is defined as EDNE-X-TARE, where X=pCAP, CAP, or Et2pCAP. All nucleofections were performed with 5 million cells in a 100 µl total volume of RPMI with no phenol red.
Figure 3C:
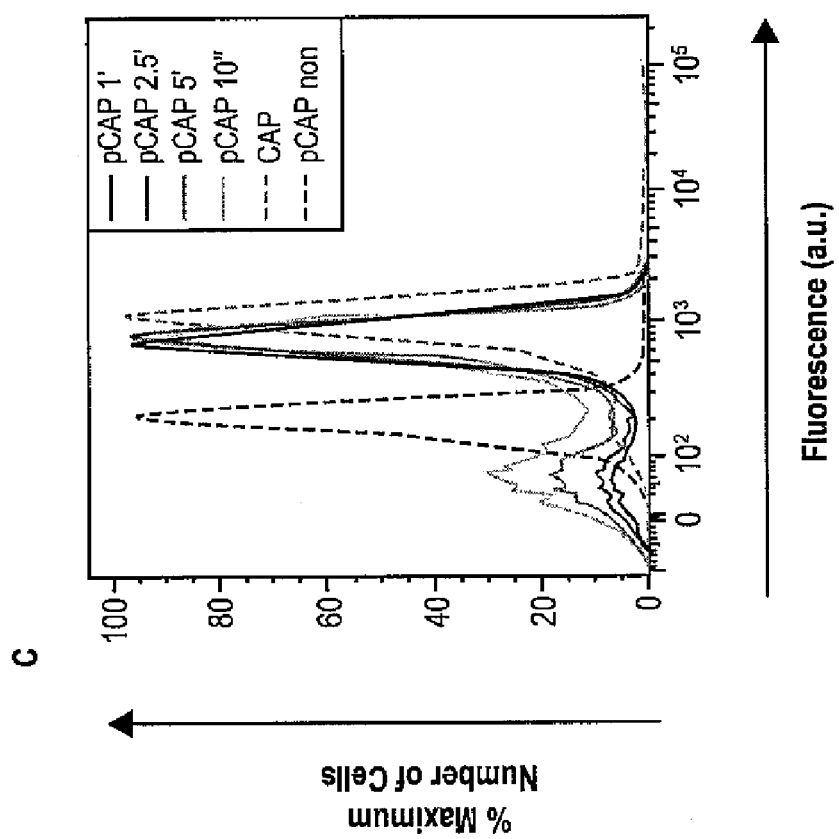
Figure 4:
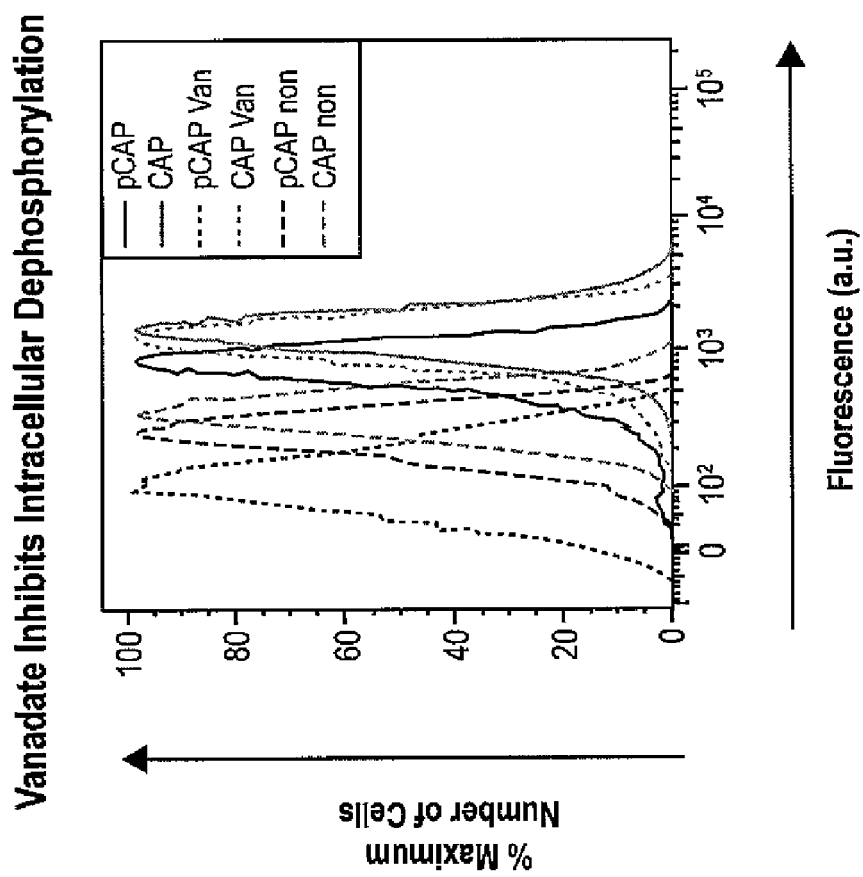
FIG. 4. Vanadate inhibits the dephosphorylation of pCAP peptide in nucleofected JTAg cells. (A) Graph shows fluorescence of cells 1' after nucleofection in the presence of 100 µM 9LckpCAP394 peptide (blue dotted and continuous lines) or 100 µM 9LckCAP394 peptide (red dotted and continuous lines) and preincubated with 10 mM vanadate (dotted lines) or buffer alone (continuous lines). Dashed red and blue lines show fluorescence of non-nucleofected cells incubated with pCAP peptide (blue dashed line) or CAP peptide (red dashed line), and vanadate.
Figures 5A, 5B:
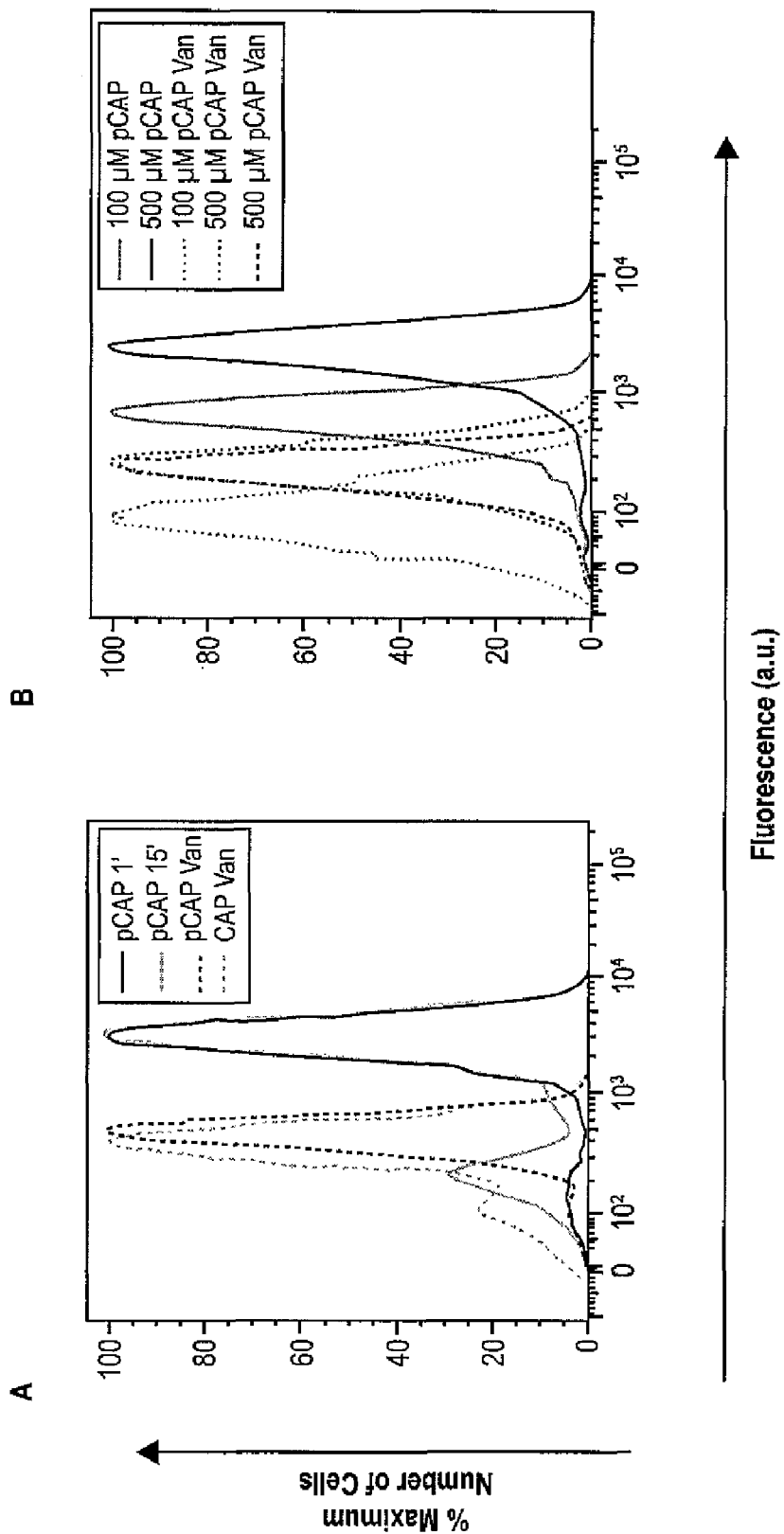
FIG. 5. Optimization of a cell-based PTP activity assay. (A) The effect of vanadate on intracellular pCAP dephosphorylation is detectable in fixed cells. Graph shows fluorescence of cells preincubated with 10 mM vanadate (dotted lines) or buffer alone (continuous lines) and fixed in 1% paraformaldehyde 1' after nucleofection in the presence of 9LckpCAP394 peptide. The fluorescence of cells was assessed at 1' (black lines) or 15' (yellow lines) after fixation. (B) High substrate concentrations improve the assay profile. Graph shows fluorescence of cells after 1' nucleofection in the presence of 100 µM 9LckpCAP394 peptide concentration (blue dotted and continuous lines) or 500 µM peptide concentration (black dotted and continuous lines) and preincubated with 10 mM vanadate (dotted lines) or buffer alone (continuous lines). The dashed black line shows fluorescence of non-nucleofected cells incubated with 500 µM peptide concentration and 10 mM vanadate.
Figure 6:
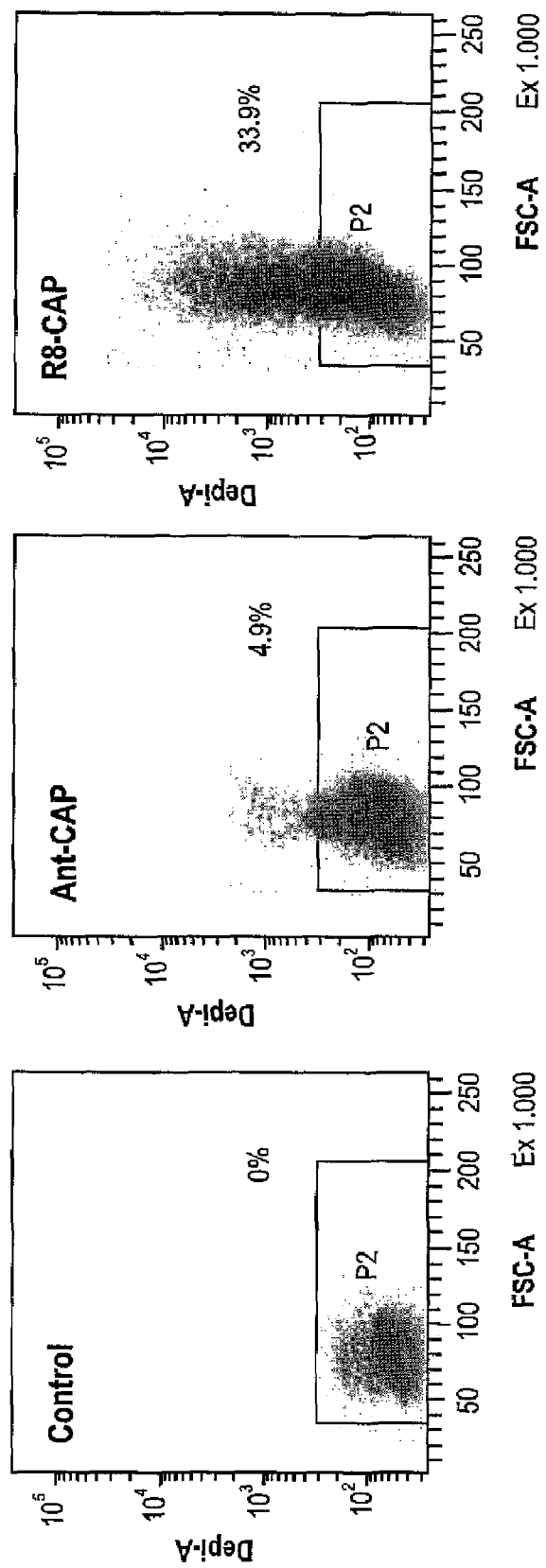
FIG. 6. R8-CAP is efficiently internalized by Jurkat-Tag T cells. Cells were incubated for 1 hour with RPMI with 0.5% FBS with DMSO alone or containing 12.5 µM of Ant-CAP or R8-CAP. The fluorescence (Y axis) versus forward scatter (X axis) of 10,000 cells gated as live T cells on the forward versus side scatter plot is shown. The percentage (%) of positive (showing fluorescence over the control level) cells is shown in each panel. Lethality (measured as % of non-gated events) was around 40% and comparable between treatments.

All of these probes are readily incorporated into peptides using standard Fmoc-based solid phase peptide synthesis methodologies.[16] Upon excitation ~340nm, the inventors found that CAP containing peptides are over $10^4$ times more fluorescent than pCAP containing peptides (emission wavelength ~460nm)[15], indicating that PTP-catalyzed hydrolysis of pCAP-containing peptides should result in a highly sensitive, fluorescent direct assay for PTP activity. The inventors recently reported that pCAP-containing peptides provide sensitive substrates for PTP activity.[15] A linear increase in fluorescence (excitation at 340 nm and emission at 460 nm) is observed when DADE-pCAP-GPAA-NH$_2$(peptide 1, SEQ ID NO: 1) is dephosphorylated by YOP, a PTP isolated from Yersinia enterocolitica. The pCAP-containing peptide 1 was also efficiently turned over by human PTPs including T cell PTP (TCPTP),[15] indicating that it could serve as a valuable probe for PTP activity in cells. The inventors have shown that pCAP peptides are dephosphorylated by PTPs, but are not recognized by serine/threonine phosphatases, which makes them particularly suitable as probes to detect intracellular PTP activity (FIG. 1). A pCAP peptide of sequence EDNE-pCAP-TARE (9Lck394p CAP), SEQ ID NO: 2), which is efficiently hydrolyzed by PTPN22, was incubated with three classes of serine-threonine phosphatases in the optimal buffer for each enzyme, and fluorescence of the reaction was monitored over time using a plate reader with excitation at 340 nm and emission at 460 nm. The amount of enzyme used was normalized to be the same activity on DiFMUP. The serine-threonine phosphatases were ineffective at hydrolysis of this peptide. To determine if these peptides are suitable substrates for cell-based screening of PTP inhibitors, the inventors further assessed dephosphorylation in microinjected cells. Using fluorescence microscopy, intracellular dephosphorylation of the microinjected peptides was observed as recognized by an increase in fluorescence over time and was inhibited by a known PTP inhibitor (FIG. 2). In order to demonstrate that flow cytometry can be used to detect intracellular dephosphorylation of the peptides, the inventors measured CAP fluorescence in flow cytometry using CAP-conjugated silica beads. The inventors found that they can detect an intense fluorescence signal analyzing the CAP beads in the FACSAria system, using the violet laser (exciting at 407 mn), and a 450/40 nm bandpass filter for detection. In principle, any FACS system equipped with the appropriate excitation and emission filters could be used. In order to demonstrate that pCAP peptide can be used to monitor intracellular PTP activity by flow cytometry, the inventors internalized pCAP peptides into JTAg cells by nucleofection and cell fluorescence was analyzed by flow cytometry. The peptides were found to be dephosphorylated in the cells and inhibition of PTP activity by a known PTP inhibitor could be detected using this method (FIGS. 3-5). The inventors believed that cell-based screening using pCAP peptides or other fluorescent PTP substrates internalized in cells and detecting cell fluorescence by flow cytometry or microscopy could yield inhibitor leads that are optimized for cell permeability and enzyme specificity and minimal cellular toxicity, thus considerably speeding up the development of therapeutic PTP inhibitors. In order to demonstrate the utility of this invention, the inventors have synthesized several cell-permeable tagged peptides for use in cellular imaging experiments, and have optimized their uptake into cells. CAP in N-terminal fusion with two types of cell-penetrating peptides (CPP), a penetratin derived from amino acids 43-58 of the Antennapedia homeodomain (ANT =RQIKIWFQNRRMKWK, SEQ ID NO: 3) and a polyarginine peptide ($R_8$) were synthesized. Human Jurkat TAg (JTAg) cells with CAP-ANT and CAP-R8 peptides were incubated and analyzed by flow cytometry. Intense cell fluorescence from internalized ANT-and R8-peptides can be easily detected by flow cytometry. In JTAg cells R8 seemed to be a more efficient CAP-peptide carrier than ANT. FIG. 6 shows cellular fluorescence after incubation of one hour with 12.5 μM Ant-CAP or R8-CAP in the presence of 0.5% serum. Several additional experiments were performed in order to optimize cellular uptake by variation of concentration of peptides and incubation buffers. For JTAg cells the inventors found that incubation of cells with 10-15 μM CAP-R8 in RPMI with 0.5%, serum for 1h leads to high cell fluorescence.

In order to increase carrier efficiency and cargo distribution in the cell cytosol, cell-permeable peptides were conjugated with lipid chains, and the cellular uptake was tested through flow cytometry and confocal microscopy. The inventors synthesized R7-CAP conjugated with N-terminal 14C and 16C lipidic chains through a beta-alanine (betaAla) spacer (C14-betaAla-R7-CAP, C16-betaAla-R7-CAP). Treatment of JTAg T cells with these lipid-R7 peptides showed that C14 and C16 were able to substantially increase efficacy of internalization as compared to the non-lipidic tags. Through confocal microscopy, the inventors found that conjugation of R7-CAP with the longer hydrocarbon chains not only increases the cellular internalization of the peptides, but also increases the cytosolic/nuclear localization ratio of cell fluorescence.

As used herein the term "cell" refers to or describes HeLa, COS, MEFs, Jurkat, Jurkat TAg (JTAg), insect cells, primary cells, or any cell with PTP activity.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

EXAMPLES

Synthesis of CAP-Related Probes and Incorporation into Peptides pCAP and the related probes CAP, mCAP, $pCAPF_n$, $CAPF_n$, and $mCAPF_n$ can be synthesized using a slight modification of the published procedure, as outlined in Scheme 1.[20,21] The pCAP residue can be incorporated into peptides using standard solid phase amino acid coupling procedures. Specifically, Rink amide resin (100 mg, $7.4 \times 1^{-5}$ mol) can be used as the solid support, and each new amino acid (5 equiv) is coupled to the growing chain using 2-(6-chloro-1-H-benzotriazole-1-yl)-l,l3,3,-tetramethyl uranium hexafluorophosphate (HCTU) as the coupling agent. In the case of the CAP-based amino acids, benzotriazol-1-oxytripyrrolidinophosphonium hexafluorophosphate (PyBOP) and N-hydroxybenzotriazole (HOBt) are more effective as coupling agents. All amino acids are allowed to couple for 1.5 h. The phosphate protecting groups on the pCAP moiety can be removed by treating the resin with 20 equiv trimethylsilyliodide (TMSI) (0.1 113 mL, 0.74 mmol) in anhydrous dichloromethane (1 mL). The beads are then washed with dichloromethane, followed by dimethylformamide (DMF). Removal of the N-terminal Fmoc group is accomplished by twice agitating the resin with 1 mL of 2% 1,8-diazabicyclo [5.4.0]undec-7-ene (DBU) in DMF. The peptides are then released from the resin under acidic conditions (1 mL of 95% trifluoroacetic acid, 2.5% $H_2O$, 2.5% triisopropylsilane) and purified twice by RP-HPLC, using either a C18 column, a diphenyl column, or both (Varian, Inc.). The resulting peptides will have acylated N-termini and amides on the C-termini. After characterization using MALDI-TOF spectrometry, stock solutions of each peptide will be made by dissolving the peptides in DMSO.

UV-Microscopy of Cells Treated with Cell-Permeable Peptides

Adherent cells (HeLa cells, Cos cells, or MEFs or any cells adherent or made to adhere to slides by any means) can be plated directly on microscope chamber slides the night before the experiment at a subconfluent density. Suspension cells (JTAg, or any other cells which spontaneously grows in suspension or is made to grow in suspension, e.g. by continuous agitation) are added to wells of a plate at a concentration of up to 10 million/mL. For incubation with the cell permeable CAP peptides, cells are washed once with PBS and resuspended in culture medium containing 0.5% serum. Equal volumes of appropriate dilutions of peptide stock solutions are added to the wells/slides in order to achieve the final concentration of peptides in the medium. After incubation in a 5% $CO_2$ incubator at 37° C. for the appropriate time, cells are washed in order to remove any non-internalized peptide. Total amount of cells, peptide concentration, peptide to cell ratio and time of incubation should be optimized for each cell type and peptide used. Cells can be imaged with a fluorescence microscope equipped with appropriate excitation and emission filters.

UV-Flow Cytometry of Cells Treated with Cell-Permeable Peptides

Cells are added to wells of a plate at a concentration of up to 10 million/mL. Cells are washed once and resuspended in culture medium containing 0.5% serum. Equal volumes of appropriate dilutions of peptide stock solutions are added to the wells/slides in order to achieve the final concentration of peptides in the medium. After incubation in a 5% $CO_2$ incubator at 37° C. for the appropriate time, cells are washed and resuspended in Hank's Balanced Salt Solution (HBSS) containing 2.5 mg/ml BSA and 5 mM EDTA and subjected to flow cytometry analysis. Total amount of cells, peptide concentration, peptide cell ratio and time of incubation should be optimized for each cell type and peptide used. Cells can be analyzed with any flow cytometry system equipped with appropriate excitation and emission filters.

Cell-Based High Throughput Screening of Small Molecule PTP Inhibitors by Flow Cytometry Cells are treated with pCAP peptides or other fluorescent PTP substrate and varying concentrations of candidate PTP inhibitors in a 96-well format, and flow cytometry analysis is performed using a UV-cytometer equipped with a multiplate, loader (MPL) system, or with a high-content fluorescence microscope. The PTP substrate can be spontaneously cell-permeable or made cell-permeable by conjugation with tags or other chemical modification. Cells are prepared for FACS analysis and assessed for inhibition of PTP activity. Amount of inhibitor and length of incubation should be analyzed for each inhibitor, substrate, and cell type used. Cells and compounds are distributed in an initial 96-well or higher number of wells plate, and a liquid handler can be used to pipette cells, compounds, and substrate in wells. The desired inhibitor will show activity in secondary cell-based assays, for example inhibitors of PTPs which negatively regulate signal transduction through a certain pathway, will show activity in western blotting assays monitoring the activation of said signal transduction pathway. If using peptide substrates, the inhibitors will also show some degree of specificity for the target phosphatase, depending on the specificity of the peptide substrate used. Also the cell-based assay in principle should detect uncompetitive and allosteric inhibitors in addition to competitive inhibitors.

pCAP peptides as specific substrates for such assays have been optimized. The novel assays can be carried out using non peptidic fluorescent PTP substrates, however pCAP-peptides offer the obvious advantages of 1) increased similarity to physiological substrates and 2) increased specificity of for PTPs versus other enzymes, and 3) the possibility of further optimizing the sequence of the peptide if needed. Thus pCAP peptides are particularly suitable as probes for the shown novel applications including cell-based HTS for PTP inhibitors.

Many modifications and variations of the invention as hereinbefore set forth can be made without departing from the spirit and scope thereof and therefore only such limitations should be imposed as are indicated by the appended claims.

All patent and literature references cited in the present specification are hereby incorporated by reference in their entirety.

REFERENCES

1. Hunter, T. Haivey Lect. 1998.94, s 1-1 19.
2. Mustelin, T.; Vang, T.; Bottini, N. Nature Rev. Immunology 2005, 5,43-57.
3. Vang, T.; Congia, M.; Macis, M. D.; Musumeci, L.; Orru, V.; Zavattari, P.: Nika, K.; Tautz, L.; Tasken. K.; Cucca, F.; Mustelin, T.: Bottini, N. Nat. Genet. 2005, 37. 1317-1319.
4. Wong, S.; Witte, O. N. Annu. Rev. Immunol. 2004, 22, 247-306.
5. Singer, A. L.; Koretzky, G. A. Science 2002, 296, 1639-40.
6. Mustelin. T.; Tasken, K. Biochem. J. 2003, 371, 15-27.
7. Tarakhovsky. A. J. Exp. Med. 2005, 201, 505-508.
8. Montalibet, J.; Skorey, K. I.: Kennedy, B. P. Methods 2005, 35, 2-8.
9. Kemp. B. E.; Pearson, R. B. Methods Enzymol. 1991, 200, 121-134.

10. Glenney, J. R. Methods Enzymol. 1991, 201, 92-100.
11. Blaydes, J. P.; Vojtesek, B.; Bloomberg, G. B.; Hupp, T.R. Methods Mol. Biol. 2000, 99, 177-1 89.
12. Harayama, H.; Muroga, M.; Miyake, M. Mol. Reprod. Dev. 2004, 69, 436-447.
13. Rink, T. J. Miner. Electrolyte Metab. 1988, 14, 7-14.
14. Mitra, S.; Barrios A. M. Analytical Biochemistry. 2007. 370, 249-251.
15. Mitra, S.; Barrios A. M. Bioorg. & Med. Chem. Lett. 2005, 15, 5142-5.
16. Camnish, L. E.: Kales, S, A. Fmoc: Solid Phase Peptide Synthesis: A Practical Approach: Oxford University Press: Oxford. 2000.
17. Sozio M S, Mathis M A, Young J A, Wälchli S, Pitcher L A, Wrage P C, Bartók B, Campbell A, Watts J D, Aebersold R, Hooft van Huijsduijnen R, van Oers N S. J Biol Chem. 2004, 279, 7760-7769.
18. Snyder et al, 2005, Nature Neuroscience, (8), 977-9

SUMMARY OF SEQUENCES

SEQUENCE LISTING
<110>Bottini, Nunzio
 Stanford, Stephanie
 Barrios, Amy
 Mitra, Sayantan
<120>Nunzio Bottini, Stephanie Stanford, Amy Barrios, and Sayanta Mitra
<130>374634-000299
<140>12/571,301
<141>2009-09-30
<150>61/101,620
<151>2008-09-30
<160>3
<170>PatentIn version 3.5
<210>1
<211>10
<212>PRT
<213>Artificial Sequence
<220>
<223>artificial YOP substrate
<220>
<221>MOD_RES
<222>(5) . . . (5)
<223>pCAP
<220>
<221>MOD_RES
<222>(10) . . . (10)
<223>NH2 group
<400>1
Asp Ala Asp Glu Xaa Gly Pro Ala Ala Xaa
1   5                           10
<210>2
<211>9
<212>PRT
<213>Artificial Sequence
<220>
<223>artificial PTPN22 substrate
<220>
<221>MOD$_{13}$ RES
<222>(5) . . . (5)
<223>pCAP
<400>2
Glu Asp Asn Glu Xaa Thr Ala Arg Glu
1   5
<210>3
<211>15
<212>PRT
<213>Artificial Sequence
<220>
<223>ANT
<400>3
Arg Gin lie Lys lie Trp Phe Gin Asn Arg Arg Met Lys Trp Lys
1   5           10              15

---

SEQUENCE LISTING

<160> NUMBER OF SEQ ID NOS: 3

<210> SEQ ID NO 1
<211> LENGTH: 9
<212> TYPE: PRT
<213> ORGANISM: Artificial Sequence
<220> FEATURE:
<223> OTHER INFORMATION: artificial YOP substrate
<220> FEATURE:
<221> NAME/KEY: MOD_RES
<222> LOCATION: (5)..(5)
<223> OTHER INFORMATION: pCAP
<220> FEATURE:
<221> NAME/KEY: MOD_RES
<222> LOCATION: (9)..(9)
<223> OTHER INFORMATION: Alanine with NH2 group

<400> SEQUENCE: 1

Asp Ala Asp Glu Xaa Gly Pro Ala Xaa
1               5

<210> SEQ ID NO 2
<211> LENGTH: 9
<212> TYPE: PRT
<213> ORGANISM: Artificial Sequence
<220> FEATURE:
<223> OTHER INFORMATION: artificial PTPN22 substrate
<220> FEATURE:

-continued

```
<221> NAME/KEY: MOD_RES
<222> LOCATION: (5)..(5)
<223> OTHER INFORMATION: pCAP

<400> SEQUENCE: 2

Glu Asp Asn Glu Xaa Thr Ala Arg Glu
1               5

<210> SEQ ID NO 3
<211> LENGTH: 15
<212> TYPE: PRT
<213> ORGANISM: Artificial Sequence
<220> FEATURE:
<223> OTHER INFORMATION: ANT

<400> SEQUENCE: 3

Arg Gln Ile Lys Ile Trp Phe Gln Asn Arg Arg Met Lys Trp Lys
1               5                   10                  15
```

What is claimed is:

1. A method of detecting intracellular protein tyrosine phosphatase (PTP) activity comprising:
   (a) obtaining one or more peptide(s), wherein said peptide(s) comprises a cell-permeable tag formed by N-terminal fusing a coumaryl-amino acid residue to a cell-permeable peptide, and wherein said coumaryl-amino acid residue may be phosphorylated coumaryl-amino propionic acid (pCAP), unphosphorylated coumary-amino propionic acid (CAP), or a fluorinated derivative thereof;
   (b) internalizing the peptides into cells and;
   (c) detecting PTP intracellular activity by monitoring cell fluorescence of the cells of step (b).

2. The method of claim 1, wherein the coumaryl amino acid residue is CAP or fluorinated derivatives thereof.

3. The method according to claim 2, wherein the cell-permeable tag is one selected from the group consisting of CAP-ANT, CAP-R8, R8-CAP and R7-CAP.

4. The method according to claim 1, wherein the cells are HeLa cells, COS cells, MEF cells, Jurkat Tag (JTAg), insect cells, or any cell with PTP activity.

5. The method according to claim 1, wherein the method further comprises internalization with serum.

6. The method according to claim 1, wherein the peptides further comprises a lipidic chain conjugated to the cell-permeable tag.

* * * * *